United States Patent [19]

Rehner et al.

[11]  4,298,498
[45]  Nov. 3, 1981

[54] CONTROL REAGENT FOR TEST STRIPS FOR DETERMINING UROBILINOGEN IN URINE

[75] Inventors: Helmut Rehner, Weilheim; Walter Rittersdorf, Mannehim-Waldhof, both of Fed. Rep. of Germany

[73] Assignee: Boehringer Mannheim GmbH, Mannheim Waldhof, Fed. Rep. of Germany

[21] Appl. No.: 103,025

[22] Filed: Dec. 13, 1979

[30] Foreign Application Priority Data

Dec. 21, 1978 [DE]  Fed. Rep. of Germany ....... 2855363

[51] Int. Cl.$^3$ .................... C09K 3/00; G01N 33/48
[52] U.S. Cl. .................. 252/408; 23/230 B; 23/901; 23/902; 23/905; 23/913; 23/929; 23/930; 422/55; 422/56
[58] Field of Search ............ 260/326.2; 252/408; 23/230 B, 905, 930, 929, 901, 902, 913; 422/55, 56

[56] References Cited

U.S. PATENT DOCUMENTS

| | | | |
|---|---|---|---|
| 2,737,501 | 3/1956 | Sherman | 252/408 |
| 3,585,001 | 6/1971 | Mast | 252/408 |
| 3,630,957 | 12/1971 | Rey et al. | 252/408 |
| 3,814,586 | 6/1974 | Fraser, Jr. et al. | 23/230 B |
| 3,850,576 | 11/1979 | Rittersdorf et al. | 23/230 B |
| 4,038,485 | 7/1977 | Johnston et al. | 252/408 |
| 4,172,049 | 10/1979 | Pfeil et al. | 252/408 |
| 4,193,766 | 3/1980 | Daunora et al. | 252/408 |

OTHER PUBLICATIONS

C.A., vol. 44, 10910ae, (1950).
C.A., vol. 71, 50354e, (1969).
C.A., vol. 76, 112,488r, (1972).
C.A., vol. 67, 120,484r, (1967).
C.A., vol. 37, 883(c), (1943).

*Primary Examiner*—Teddy S. Gron
*Attorney, Agent, or Firm*—Sprung, Felfe, Horn, Lynch & Kramer

[57]  ABSTRACT

The present invention provides a control reagent for test strips for the detection of urobilinogen and possibly of other diagnostically relevant components, such as bilirubin, ketone bodies, glucose, protein, nitrite and blood, and possibly also of pH, which has a content of 2,4-dimethylpyrrole-3-carboxylic acid and/or of at least one alkali metal and/or alkaline earth metal salt thereof as control substance for urobilinogen.

14 Claims, No Drawings

CONTROL REAGENT FOR TEST STRIPS FOR DETERMINING UROBILINOGEN IN URINE

This invention relates to a control reagent, more particularly, to a control solution for test strips for the detection of urobilinogen and optionally other relevant components of urine.

Test strips are used to an increasing extent for the routine investigation of urine. Test strips are to be understood to be solid carrier materials in the form of strips, rods or the like which contain reagents and which, upon dipping into the solutions to be investigated, give characteristic color reactions which can be purely qualitative or can also be semi-quantitative or quantitative. In the case of such test strips, from time to time it is necessary to carry out a functional control in order to keep the percentage of the falsely negative findings as small as possible. For this functional control, it is preferable to use a so-called control urine.

These control urines usually consist of pooled human urines which, by augmenting and/or supplementing with desired urine components, is often converted into a "pathological" urine. For reasons of storage stability, the control urine (hereinafter called a control reagent) is usually freeze-dried. For use, reconstitution is carried out with water or a diluent, which often contains acetone and/or stabilized erythrocytes. The reconstituted control reagent is then a control solution which is ready for use, i.e., the control urine.

Instead of using human urine as a basis for the control reagent, use can also be made of an artificial, buffered mixture which should approximate as far as possible to the properties of human urine. Artificial urines are known and commercially available in the form of ready-to-use solutions and in the form of tablets and powder.

Urobilinogen is one of the diagnostically relevant components of urine. The detection of urobilinogen in urine, which usually takes place by azo coupling with a p-methoxybenzene-diazonium salt, serves for the recognition of liver and haemolytic diseases. However, most of the known control urines do not contain urobilinogen because this compound is very unstable. Therefore, attempts have already been made to replace urobilinogen by some other compound which reacts like urobilinogen but is also stable.

An artificial control reagent (control urine) is already known which contains an organic compound as a substitute for urobilinogen but which reacts with a different reaction color on the urobilinogen test field of the appropriate test strip than urobilinogen itself. This makes a quantitative concentration estimation of this parameter impossible since a color comparison cannot be carried out. Therefore, in the functional test, only a yes-no decision is possible.

It is an object of the present invention to provide a control reagent for test strips for urine investigations which are suitable for the detection of urobilinogen, which reagent contains, for the urobilinogen functional control, a stable substance which is different from urobilinogen, which substance gives a reaction color on the urobilinogen test field which is directly comparable with the urobilinogen coloration and, therefore, makes possible a quantitative concentration estimation.

In particular, it is an object of the present invention to provide a control reagent of the above-described type which contains a substitute for urobilinogen, which behaves analogously to urobilinogen in the detection system for urobilinogen by azo coupling with a p-methoxybenzene-diazonium salt and which does not have a disturbing effect in the case of the simultaneous presence of a detection system for bilirubin based upon azo coupling with a 2,6-dichlorobenzenediazonium salt.

Surprisingly, we have found that 2,4-dimethylpyrrole-3-carboxylic acid and the alkali metal and alkaline earth metal salts thereof, preferably the sodium salt, can be used as an ideal substitute in the above-mentioned type of control reagent for urobilinogen with regard to reactivity, color formation and sensitivity. It is especially surprising that this compound does not react with the more active 2,6-dichlorobenzene-diazonium salt, which serves for the detection of bilirubin and, therefore, does not disturb by simulating a content of bilirubin.

An investigation of the stability of this compound showed that not only the free 2,4-dimethylpyrrole-3-carboxylic acid but also the mentioned salts thereof, especially the alkali metal salts and particularly the sodium salt, have a sufficient stability and, therefore, constitute an ideal substitute for the unstable urobilinogen in control reagents of the above-mentioned type.

Thus, according to the present invention, there is provided a control reagent for test strips for the detection of urobilinogen and possibly of other diagnostically relevant components, such as bilirubin, ketone bodies, glucose, protein, nitrite and blood, and possibly also of pH, which has a content of 2,4-dimethylpyrrole-3-carboxylic acid and/or of at least one alkali metal and/or alkaline earth metal salt thereof as control substance for urobilinogen.

In a preferred embodiment, the reagent according to the present invention contains aluminium, magnesium and/or beryllium acetylacetonate as ketone body substitute. These compounds are sufficiently stable, are not hydrolyzed at the pH values in question, do not give rise to the formation of water-insoluble metal hydroxides and do not disturb the urobilinogen detection. The aluminium compound is especially preferred. The above-mentioned acetylacetonates are practically colorless.

The control reagent according to the present invention preferably also contains definite amounts of the other components of urine which are usually regarded as being diagnostically relevant. Particular mention is made of nitrite, protein, glucose, blood (haemoglobin) and buffer substances for the testing of the pH value determination. The nitrite is a readily soluble alkali metal or alkaline earth metal nitrite, preferably sodium nitrite. The protein is preferably albumin, for example bovine albumin.

Glucose is preferably used in the form of D(+)-glucose and bilirubin in the form of a soluble salt, especially the sodium salt. For the blood parameter, it is preferable to use haemoglobin, for example bovine haemoglobin.

The buffer substances used can, in principle, be any of those which are conventional and buffer in the pH range of from 7.5 to 9.0. Examples of buffers which can be used include triethanolamine/hydrochloric acid, sodium pyrophosphate/hydrochloric acid, sodium diethylbarbiturate/hydrochloric acid, tris-(hydroxymethyl)-aminomethane/hydrochloric acid, borax/boric acid, sodium borate/hydrochloric acid, a Good's Zwitterionic buffer, such as N,N-bis-(2-hydroxyethyl)-glycine, N-[tris-(hydroxymethyl)-methyl]-glycine or 2-[4-(2-hydroxyethyl)-piperazin-1-yl]-ethanesulphonic acid.

A preferred buffer capacity is from 5 to 25 mMol/liter of solution.

A preferred composition of the control reagent according to the present invention preferably consists essentially of:

0.002 to 0.4 g. 2,4-dimethylpyrrole-3-carboxylic acid,
0 to 0.1 g. of a bilirubin salt,
0 to 5.0 g. aluminium acetylacetonate or of an equivalent amount of the corresponding magnesium or beryllium compound,
0 to 0.1 g. nitrite,
0 to 7 g. albumin,
0 to 0.1 g. haemoglobin,
0.3 to 100 g. buffer substance, pH 7.5 to 9.0, in solid or dissolved form, referred to 1 liter of solution ready for use.

A particularly preferred composition consists of:
0.007 to 0.2 g. 2,4-dimethylpyrrole-3-carboxylic acid,
0 to 0.07 g. of a bilirubin salt,
0 to 2.0 g. aluminium acetylacetonate or of an equivalent amount of the corresponding magnesium or beryllium compound,
0 to 0.01 g. nitrite,
0 to 3.0 g. albumin,
0 to 3.0 g. D(+)-glucose,
0 to 0.04 g. haemoglobin,
0.3 to 25 g. buffer substance, pH 7.8 to 8.5, in solid or dissolved form, referred to 1 liter of solution.

In the above-mentioned reagents, the given amounts refer to the amounts of solid intended for dissolving in 1 liter of water or to the content of 1 liter of final control reagent solution (artificial urine). It is, of course, to be understood that the reagent can also contain a multiple or a fraction of the above-described compositions, provided that the relationship of the amounts of the individual components remain within the given ranges. A preferred buffer is sodium diethylbarbiturate/diethylbarbituric acid.

Furthermore, the control reagent according to the present invention can also contain further components which are known for control urines, for example, other sugars, ascorbic acid, coloring materials, hormones, urea, enzymes and the like. In addition, tabletting adjuvants, filling agents, binding agents, stabilizers, for example antioxidants, and/or lubricants can also be added.

The superior stability of the control reagent according to the present invention containing 2,4-dimethylpyrrole-3-carboxylic acid or the sodium salt thereof, in comparison with the sodium salt of urobilinogen, is shown by the following Table. The stability investigations were carried out on solutions obtained by dissolving reagent tablets which also contain, apart from the substances mentioned in the Table, sodium nitrite, buffer (pH 3.0), bovine serum albumin, glucose, sodium bilirubinate, aluminium acetylacetonate and bovine haemoglobin.

TABLE

| substance | initial value mg./100 ml. = 100% | change of concentration (%) in the case of storage at 35° C. | | | | |
|---|---|---|---|---|---|---|
| | | 1 wk. | 2 wks. | 3 wks. | 6 wks. | 12 wks. |
| sodium salt of urobilinogen | 7.87 | −43 | −57 | −64 | | |
| 2,4-dimethyl-pyrrole-3-carboxylic acid sodium 2,4-dimethyl-pyrrole-3-carboxylate | 6.59 7.99 | −1 +6 | −1 +6 | −1 +5 | −4 −3 | −8 −7 |

The above values show the superiority of the control reagent according to the present invention with regard to stability in comparison with a urobilinogen-containing reagent of the same composition. Furthermore, the control reagent according to the present invention has the advantage of making possible a quantitative estimation of the urobilinogen content by comparison with the color developed in the case of the azo coupling of the 2,4-dimethylpyrrole-3-carboxylic acid component. A further advantage is that the detection of bilirubin is not impaired. In the preferred embodiment, there is yet the further advantage that the control of the ketone body detection reaction is also possible without disturbance of other detection reactions and without reduction of the stability of the reagent.

The following Example is given for the purpose of illustrating the present invention:

EXAMPLE

The following Table shows the composition of a control reagent according to the present invention in the form of a tablet which is intended to be dissolved in 15 ml. water to give a control solution ready for use:

| parameter | substance | amount/tablet |
|---|---|---|
| nitrite | sodium nitrite | 0.0675 mg. |
| pH value | sodium diethylbarbiturate/ diethylbarbituric acid | 26 mg./32 mg. (pH 8.0) |
| protein | albumin | 15.000 mg. |
| glucose | D(+)-glucose | 15.000 mg. |
| ketone bodies | aluminum acetylacetonate | 8.10 mg. |
| urobilinogen | sodium 2,4-dimethyl-pyrrole-3-carboxylate | 2.200 mg. |
| bilirubin | sodium metal salt of bilirubin | 0.5221 mg. |
| blood | haemoglobin | 0.0200 mg. |

It will be understood that the specification and examples are illustrative, but not limitative of the present invention and that other embodiments within the spirit and scope of the invention will suggest themselves to those skilled in the art.

We claim:

1. An artificial human urine control reagent for analytical test strips used in analyzing human urine, comprising a mixture of a component selected from 2,4-dimethylpyrrole-3-carboxylic acid, alkali metal salts thereof and alkaline earth metal salts thereof as a substitute for naturally occurring urobilinogen in human urine and at least one other component which is or simulates a diagnostically relevant component of human urine, the ratio of urobilinogen substitute to said other at least one component simulating conditions naturally occurring in human urine.

2. Control reagent as claimed in claim 1 wherein said 2,4-dimethylpyrrole-3-carboxylic acid component is 2,4-dimethylpyrrole-3-carboxylic acid.

3. Control reagent as claimed in claim 1 wherein said 2,4-dimethylpyrrole-3-carboxylic acid component is in solid form.

4. Control reagent as claimed in claim 1 wherein said 2,4-dimethylpyrrole-3-carboxylic acid component is in dissolved form.

5. Control reagent as claimed in claim 1 also comprising a buffer substance.

6. Control reagent as claimed in claim 1 wherein said test strip is for the detection of urobilinogen.

7. Control reagent as claimed in claim 6 wherein said test strip is for the detection of urobilinogen and, optionally, of other diagnostically relevant components.

8. Control reagent as claimed in claim 7 wherein such other diagnostically relevant components are bilirubin, ketone bodies, glucose, protein, nitrite, blood and pH.

9. Control reagent as claimed in claim 1 comprising
0.002 to 0.4 g. 2,4-dimethylpyrrole-3-carboxylic acid,
0 to 0.1 g. bilirubin salt,
0 to 5.0 g. aluminium acetylacetonate or an equivalent amount of the corresponding magnesium or beryllium compound,
0 to 0.1 g. nitrite,
0 to 7 g. albumin,
0 to 0.1 g. haemoglobin,
0.3 to 100 g. buffer substance, pH 7.5 to 9.0,
in solid or dissolved form, referred to 1 liter of solution.

10. Control reagent as claimed in claim 1 comprising
0.007 to 0.2 g. 2,4-dimethylpyrrole-3-carboxylic acid,
0 to 0.07 g. bilirubin salt,
0 to 2.0 g. aluminium acetylacetonate or an equivalent amount of the corresponding magnesium or beryllium salt,
0 to 0.01 g. nitrite,
0 to 3.0 g. albumin,
0 to 3.0 g. D(+)-glucose,
0 to 0.04 g. haemoglobin,
3 to 25 g. buffer substance, pH 7.8 to 6.5,
in solid or dissolved form, referred to 1 liter of solution.

11. Control reagent as claimed in claim 1 wherein the 2,4-dimethylpyrrole-3-carboxylic acid is used in the form of its sodium salt.

12. Control reagent as claimed in claim 5 wherein the buffer substance used has a buffer capacity of 5 to 25 mMol/liter.

13. Control reagent as claimed in claim 5 wherein the buffer substance used is sodium diethylbarbiturate/diethylbarbituric acid.

14. Control reagent as claimed in claim 1 in tablet form.

* * * * *

UNITED STATES PATENT AND TRADEMARK OFFICE
CERTIFICATE OF CORRECTION

PATENT NO. : 4,298,498

DATED : Nov. 3, 1981

INVENTOR(S) : Helmut Rehner et al

It is certified that error appears in the above–identified patent and that said Letters Patent are hereby corrected as shown below:

Column 6, line 13   Delete "6.5" and insert --8.5--.

Signed and Sealed this

Twentieth Day of April 1982

|SEAL|

Attest:

GERALD J. MOSSINGHOFF

*Attesting Officer*    *Commissioner of Patents and Trademarks*